(12) United States Patent
Rao et al.

(10) Patent No.: US 12,318,239 B2
(45) Date of Patent: Jun. 3, 2025

(54) X-RAY LEAD MARKER DETECTION SYSTEM FOR X-RAY IMAGING SYSTEM

(71) Applicant: GE Precision Healthcare LLC, Wauwatosa, WI (US)

(72) Inventors: Gireesha Chinthamani Rao, Pewaukee, WI (US); Ravi Soni, San Ramon, CA (US); Poonam Dalal, Brookfield, WI (US); Chen Liu, Mountain View, CA (US); Dibyajyoti Pati, Dublin, CA (US); Katelyn Nye, Glendale, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 341 days.

(21) Appl. No.: 17/975,878

(22) Filed: Oct. 28, 2022

(65) Prior Publication Data
US 2023/0165555 A1    Jun. 1, 2023

Related U.S. Application Data

(60) Provisional application No. 63/283,347, filed on Nov. 26, 2021.

(51) Int. Cl.
*A61B 6/50* (2024.01)
*A61B 6/00* (2006.01)
(Continued)

(52) U.S. Cl.
CPC .............. *A61B 6/52* (2013.01); *A61B 6/5294* (2013.01); *A61B 6/58* (2013.01); *A61B 6/587* (2013.01);
(Continued)

(58) Field of Classification Search
CPC ........... A61B 6/40; A61B 6/52; A61B 6/5294; A61B 6/545; A61B 6/58; A61B 6/582; A61B 6/587; G16H 30/40; G16H 50/20
See application file for complete search history.

(56) References Cited

U.S. PATENT DOCUMENTS

| | | | |
|---|---|---|---|
| 2011/0123074 A1 | 5/2011 | Nie | |
| 2021/0271931 A1* | 9/2021 | Younis | ................... G16H 30/20 |
| 2021/0350186 A1* | 11/2021 | Younis | ..................... G06N 3/08 |

FOREIGN PATENT DOCUMENTS

| | | |
|---|---|---|
| EP | 3872757 A1 | 9/2021 |
| WO | 2020219193 A1 | 10/2020 |

OTHER PUBLICATIONS

Ross W. Filce et al., Effectiveness of Deep Learning Algorithms to Determine Laterality in Radiographs, J Digit Imaging 32, 656-664, May 7, 2019.
(Continued)

*Primary Examiner* — Mark R Gaworecki
(74) *Attorney, Agent, or Firm* — Boyle Frederickson S.C (57) ABSTRACT

An artificial intelligence (AI) lead marker detection system is employed either as a component of the X-ray imaging system or separately from the X-ray imaging system to scan post-exposure X-ray images to detect and insert various lead markers, to digitize information provided by the type and location of the lead marker, and to employ the marker information in different X-ray system workflow automations. The marker information obtained by the AI lead marker detection system can also provide useful data for use in downstream clinical and quality applications apart from the X-ray system, such as either AI or non-AI analytical applications.

20 Claims, 6 Drawing Sheets

(51) Int. Cl.
   *A61B 6/40*   (2024.01)
   *A61B 6/58*   (2024.01)
   *G16H 30/40*  (2018.01)
   *G16H 50/20*  (2018.01)

(52) U.S. Cl.
   CPC .............. *G16H 30/40* (2018.01); *A61B 6/40* (2013.01); *A61B 6/545* (2013.01); *A61B 6/582* (2013.01); *G16H 50/20* (2018.01)

(56) References Cited

OTHER PUBLICATIONS

Christian Jamtheim Gustafsson et al., Development and valuation of a deep learning based artificial intelligence for automatic identification of gold fiducial markers in an MRI-only prostate radiotherapy workflow, 2020 Phys. Med. Biol. 65 225011.
EP application 22207481.7 filed Nov. 15, 2022—extended Search Report issued Apr. 13, 2023; 8 pages.

* cited by examiner

X-RAY LEAD MARKER DETECTION SYSTEM FOR X-RAY IMAGING SYSTEM

CROSS-REFERENCE TO RELATED APPLICATIONS

The present application claims priority from U.S. Provisional Patent Application Ser. No. 63/283,347, filed on Nov. 26, 2021, the entirety of which is expressly incorporated by reference herein for all purposes.

FIELD OF THE DISCLOSURE

The present disclosure relates to X-ray imaging systems, and more particularly to X-ray imaging systems including ancillary image processing systems to improve quality of images produced by the X-ray systems.

BACKGROUND OF THE DISCLOSURE

A number of X-ray imaging systems of various designs are known and are presently in use. Such systems are generally based upon generation of X-rays that are directed toward a subject of interest. The X-rays traverse the subject and impinge on a detector, for example, a film, an imaging plate, or a portable cassette. The detector detects the X-rays, which are attenuated, scattered or absorbed by the intervening structures of the subject. In medical imaging contexts, for example, such systems may be used to visualize the internal structures, tissues and organs of a subject for the purpose screening or diagnosing ailments.

It is a common practice for radiographers to use indicators, such as lead markers during x-ray radiographic imaging using the X-ray systems. The lead markers are readily discernable within the images output by the X-ray systems and generally serve as an easy way to indicate the left-right orientation of the subject of the x-ray, as well as other important details, such as body position, time of procedure and the initials of the radiographer performing the X-ray etc., directly within the image produced by the X-ray system.

In particular, the lead markers operate as concrete, easily legible additions to x-ray images that add valuable information about the patient, radiographer and the procedure that was performed. They not only help reduce errors and liabilities for radiographers, but it is effective way for them to highlight important aspects of the anatomy for diagnosticians and clarify the purpose of that specific image. As a result, many hospitals now require radiographers to use X-ray lead markers while performing an X-ray imaging process in order to accurately record information about the procedure performed, not only to improve image readability but also for legal and accurate documentation purposes.

However, the process for positioning the lead markers requires the X-ray technician to manually select and place the appropriate marker(s) adjacent the anatomy of the patient being imaged. As a result, often the X-ray technician or radiographer can misplace the x-ray markers with regard the anatomy being imaged, may utilize the incorrect lead marker for the particular image, or may fail to place a lead marker within the area to be imaged at all. In the situation where the marker was not positioned within the image at all, the technician may also fail to notice the error in the image and not take advantage of post-exposure markers that available for their use to include in the image.

Therefore, it is desirable to develop a system and method for detecting the presence of lead markers in a post-exposure X-ray image on an X-ray imaging system that enables errors concerning the presence, location and/or information provided by the lead marker to be corrected in the post-exposure image that overcomes these limitations of the prior art.

SUMMARY OF THE DISCLOSURE

According to one aspect of an exemplary embodiment of the disclosure, an artificial intelligence (AI) lead marker detection system is employed either as a component of the X-ray imaging system or separately from the X-ray imaging system to scan post-exposure X-ray images to detect and insert various lead markers, to digitize information provided by the type and location of the lead marker, and to employ the marker information in different X-ray system workflow automations. The marker information obtained by the AI lead marker detection system can also provide useful data for use in downstream clinical and quality applications apart from the X-ray system, such as either AI or non-AI analytical applications.

According to another aspect of an exemplary embodiment of the disclosure, the AI lead marker detection system detects both or either of the presence and/or the absence of lead markers within the post-exposure X-ray image. The AI lead marker detection system, in conjunction with information regarding selected clinical protocols, and available sensor information from devices operably connected to the X-ray system, such as a camera, can enable the AI lead marker detection system to provide quality checks for the post-exposure X-ray images.

According to another aspect of an exemplary embodiment of the disclosure, the AI lead marker detection system can operate to add an appropriate lead marker to the post-exposure X-ray image for clarity and diagnosis accuracy.

According to yet another aspect of an exemplary embodiment of the present disclosure, an X-ray system includes an X-ray source, an X-ray detector positionable in alignment with the X-ray ray source, and a processing unit operably connected to the X-ray source and the X-ray detector to produce X-ray images from data transmitted from the X-ray detector, wherein the processing unit includes lead marker detection system configured to detect a presence or an absence of representations of physical lead markers within the X-ray images.

According to still a further aspect of an exemplary embodiment of the present disclosure, a method of determining the presence of lead markers in an X-ray image includes the steps of providing an X-ray system having X-ray source, an X-ray detector positionable in alignment with the X-ray ray source and a processing unit operably connected to the X-ray source and the X-ray detector to produce X-ray images from data transmitted from the X-ray detector, wherein the processing unit includes a lead marker detection system configured to detect representations of physical lead markers in the X-ray images, and applying the lead marker detection system to the X-ray images.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Figure 1:
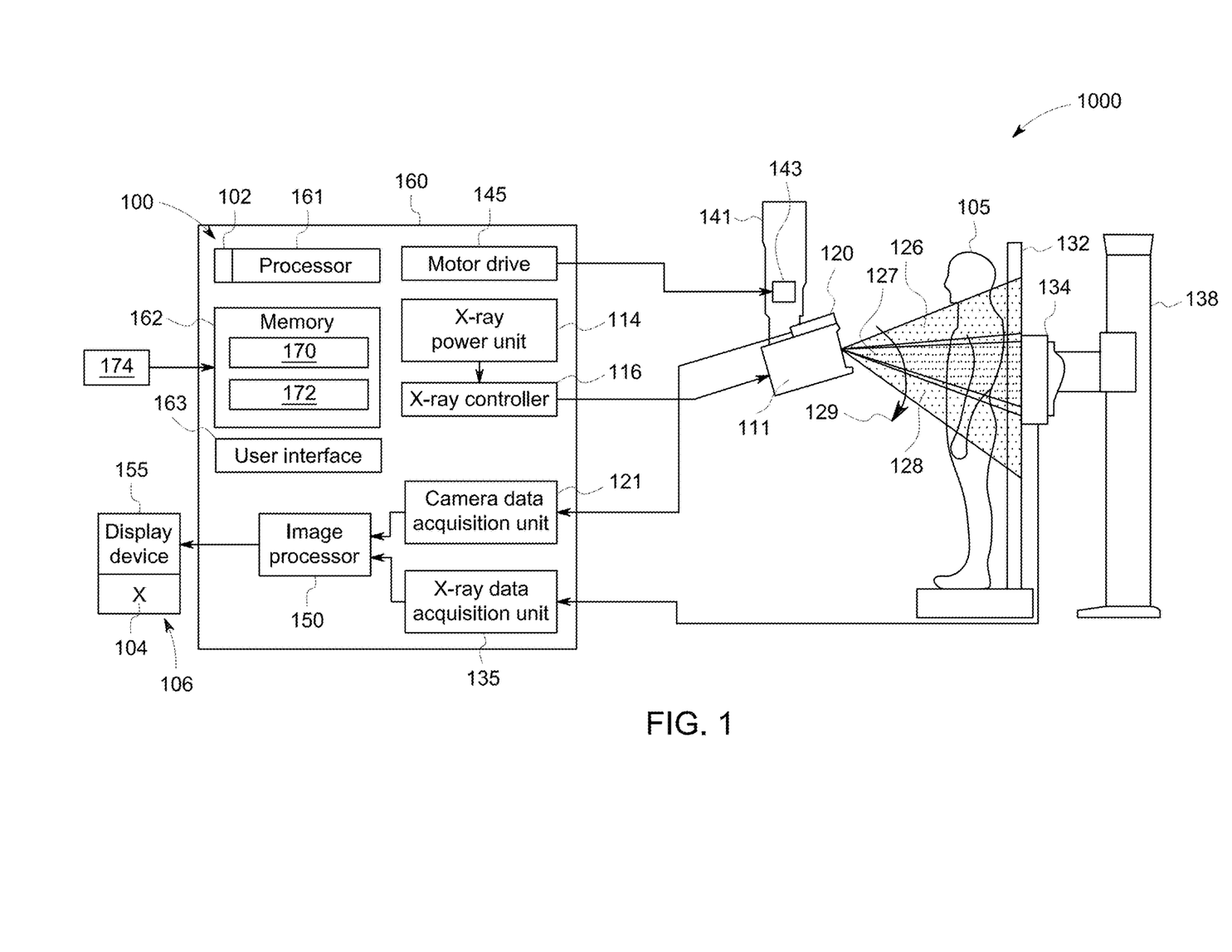
FIG. 1 is a schematic view of an X-ray imaging system employing the AI lead marker detection system according to an exemplary embodiment of the disclosure.

Referring to FIG. 1, a block diagram of an exemplary x-ray imaging system 1000 in accordance with an illustrated exemplary embodiment is shown. The x-ray imaging system 1000 includes an x-ray source 111 which radiates x-rays, a stand 132 upon which the subject 105 stands during an examination, and an x-ray detector 134 for detecting x-rays radiated by the x-ray source 111 and attenuated by the subject 105. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 160 comprises a processor 161, a memory 162, a user interface 163, a motor drive 145 for controlling one or more motors 143, an x-ray power unit 114, an x-ray controller 116, a camera data acquisition unit 121, an x-ray data acquisition unit 135, and an image processor 150. X-ray image data transmitted from the x-ray detector 134 is received by the x-ray data acquisition unit 135. The collected x-ray image data are image-processed by the image processor 150. A display device 155 communicatively coupled to the operating console 160 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 105. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 145 of the operation console 160 may be communicatively coupled to the one or more motors 143 and configured to control the one or more motors 143. The one or more motors 143 may further be configured to adjust an angular position of the x-ray source 111 to change a field-of-view of the x-ray source 111, as described further herein.

The x-ray power unit 114 and the x-ray controller 116 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

The x-ray source 111 and the camera 120 may pivot or rotate relative to the support post 141 in an angular direction 129 to image different portions of the subject 105.

Memory 162 stores image data/x-ray images 106 in electronic storage location 170 and executable instructions in electronic storage location 172 that when executed cause one or more of the processor 161 and the image processor 150 to perform one or more actions. Example methods that may be stored as the executable instructions 172 are described further herein with regard to the lead marker detection system 100 and AI application 102 of FIGS. 1 and 2.

The processor 161 additionally includes a lead marker detection system 100. The lead marker detection system 100 is formed by an artificial intelligence (AI) application 102 that can scan and detect the representation of various physical x-ray lead markers 104 (FIGS. 1 and 3) in a post-exposure X-ray image 106 (FIGS. 1 and 3). The AI application 102, which can be a deep learning neural network, is an image-based object detection application that is configured for the detection and digitization of a lead marker 104 in the post-exposure X-ray image 106, as well as the information provided by any lead marker 104 present in the X-ray image 106, such as information provided by the position, shape and/or configuration of the lead marker 104 in the X-ray image 106. The AI application 102 employs that information in various manners. For example, when a lead marker 104 is not detected within the X-ray image 106, the AI application 102 can alert the radiographer of the omitted lead markers 104 in the X-ray image 106, and may assist in the decision of the radiographer to either retake the exposure with the proper lead marker 104 or to insert a post-exposure digital lead marker 104 into the X-ray image 106.

The information obtained by the AI application 102 regarding the representations of the physical lead markers 104 present in the X-ray image 106 can also be used in conjunction with other AI algorithms (not shown) either contained on the X-ray system 1000 or employed separate from the X-ray system 1000 to automatically detect the correct location and placement for the lead marker 104 within the X-ray image 106. As such, the digitization of the lead marker 104 located by the AI application 102 for inclusion on or in association with the x-ray image 106 enables the lead marker 104 to automatically be properly repositioned within the X-ray image 106 as a digital marker 104 thereby saving additional user interface clicks and speeding up workflow and further processing of the X-ray image 106.

The information obtained by the AI application 102 from the detection and digitization of the lead marker 104 can also be aggregated with information from other sensors (such as a camera) and analytical information available to the AI application 102 concerning the context of x-ray exam to automate and simplify the workflow for the post-exposure processing of the X-ray image 106 by the radiographer. At the same time this data aggregation can ensure that the most complete and accurate information is recorded in association with the X-ray image 106 the image to help radiologists reading/reviewing the X-ray image 106 to make an accurate diagnosis.

Figure 2:
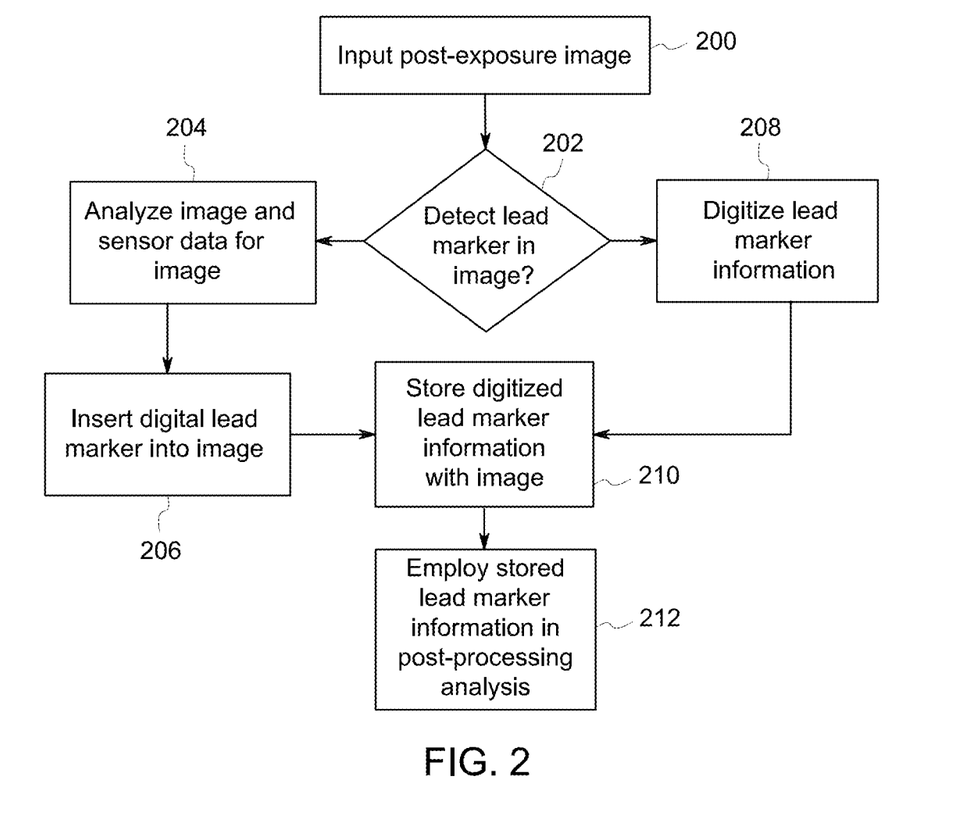
FIG. 2 is a flowchart of a method of operation of the AI lead marker detection system according to an exemplary embodiment of the disclosure.
Figure 3A:
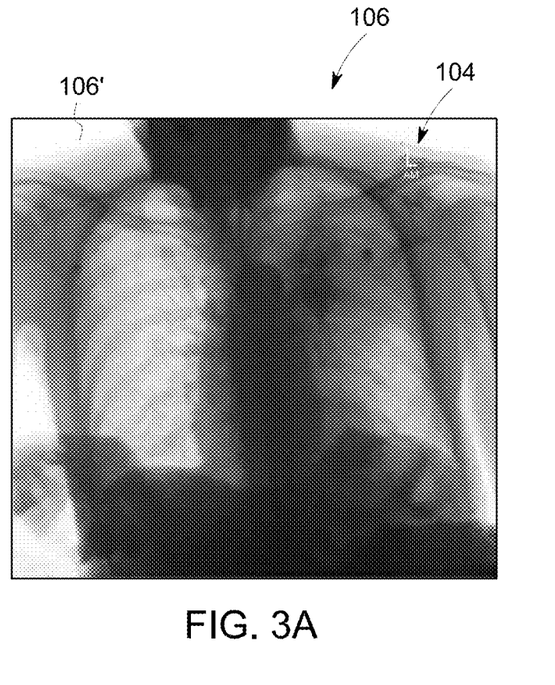
FIGS. 3A-3H illustrate matched pairs of post-exposure X-ray images prior to and after analysis by the AI lead marker detection system according to an exemplary embodiment of the disclosure.
Figure 3B:
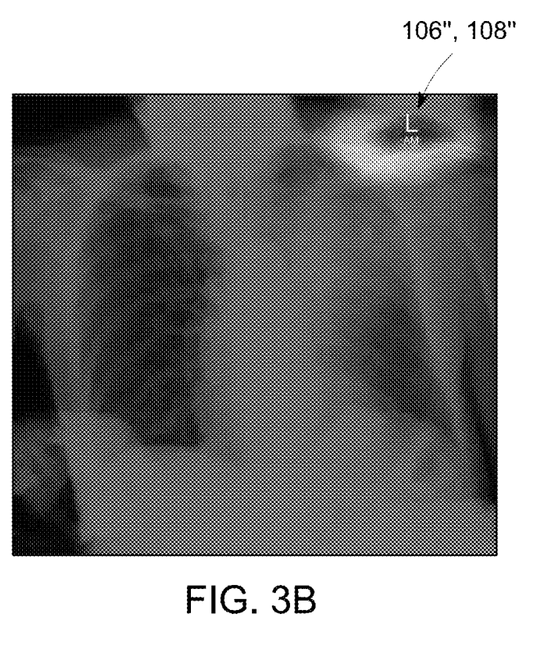
Figure 3C:
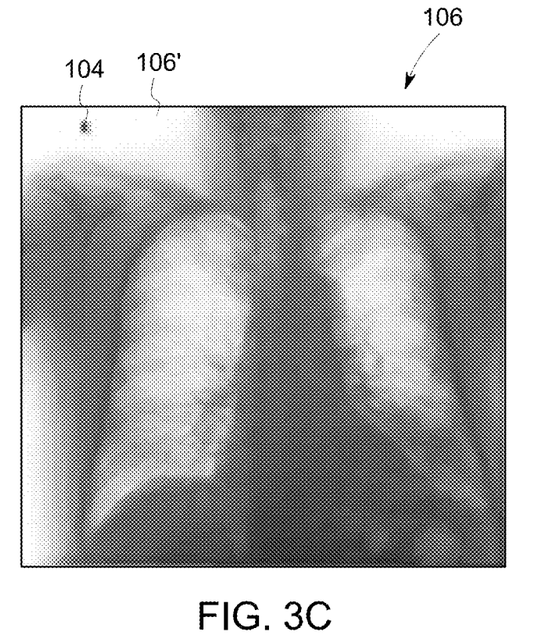
Figure 3D:
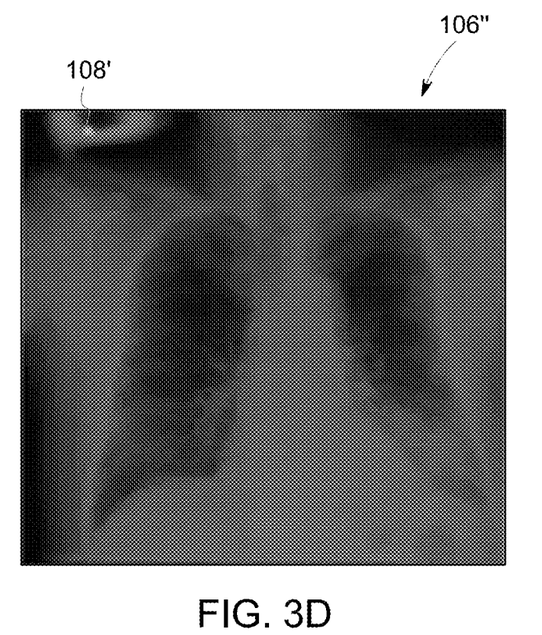
Figure 3E:
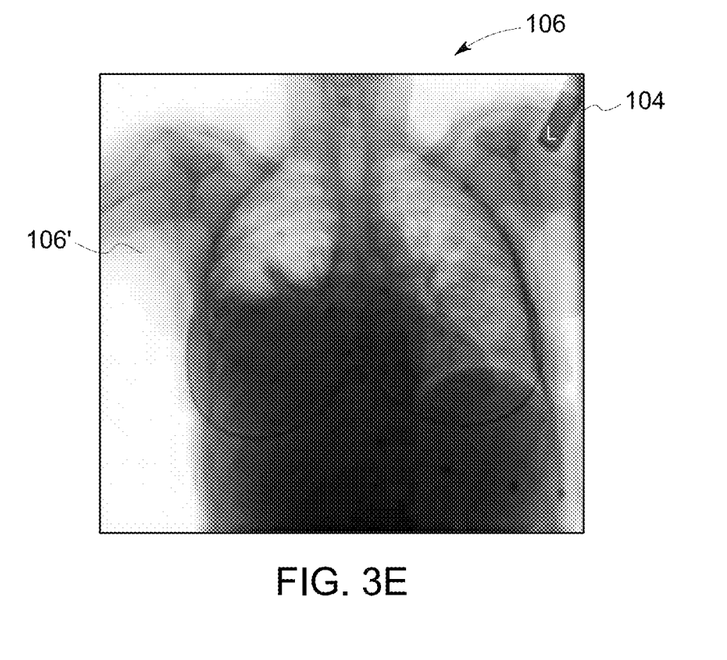
Figure 3F:
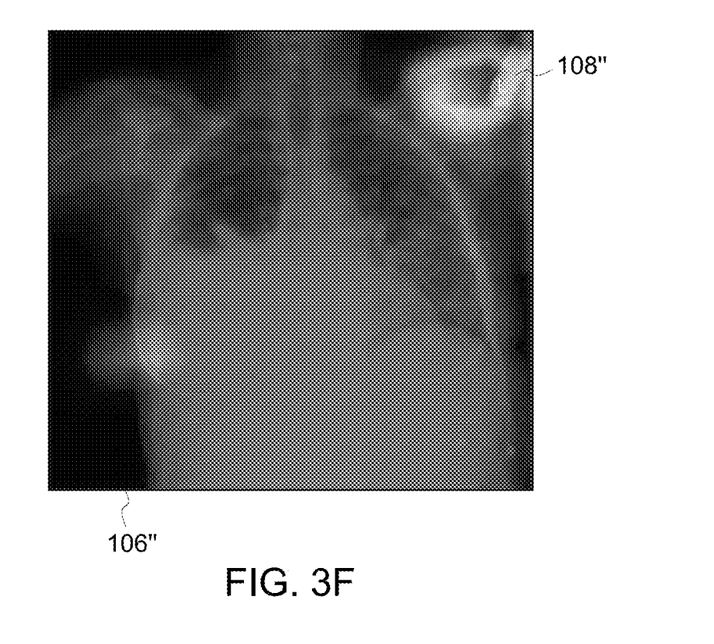
Figure 3G:
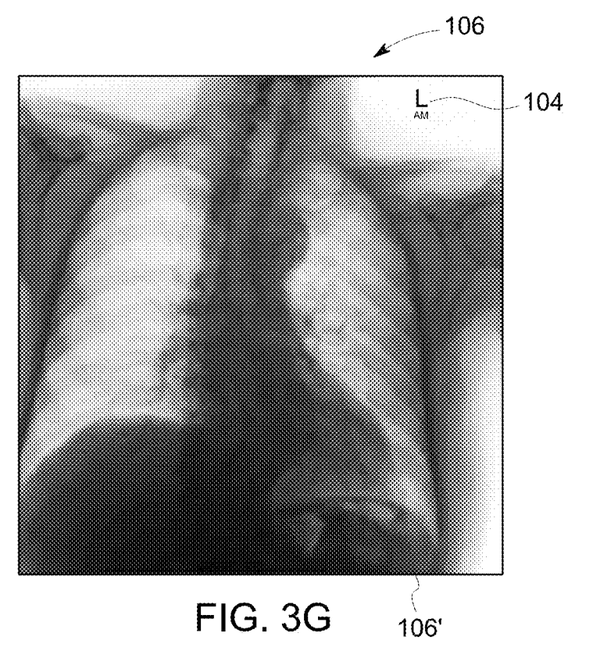
Figure 3H:
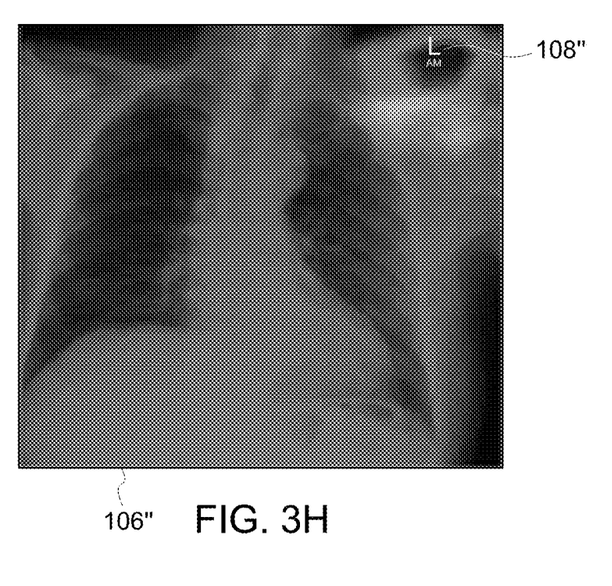

Referring now to FIG. 2, in an exemplary embodiment of the method of operation of the lead marker detection system 1000, initially in block 200 the lead marker detection system 100 is provided with an X-ray image 106 produced by the X-ray system 1000. In decision block 202, the AI application 102 of the lead marker detection system 100 analyzes the X-ray image 106 to determine the presence and/or absence of the representations of any physical lead markers 104 within the X-ray image 106.

If the AI application does not detect a lead marker 104 within the X-ray image 106, in block 204 the AI application 102 will analyze various characteristics and other information relating to the X-ray image 106 to determine what lead markers should be present in the X-ray image 106. These characteristics and information can include, but are not limited to, the anatomy and laterality thereof determined to be present within the X-ray image 106, and/or the view and/or orientation of the X-ray image 106 of the detected anatomy, among others. Once determined, such as by using any suitable image analysis algorithms (not shown) located on or operably connected to the system 1000 and/or forming a part of the AI application 102, the AI application 102 can proceed to block 206 to insert the required marker(s) 104 digitally within the image 106 for review and confirmation by the technician.

The information from the lead marker 104 either detected (block 208) or inserted into the image 106 by the AI application 102 is subsequently stored in association with the image 106 in block 210, such as in electronic storage location 170 within the x-ray system 1000 and/or in a separate storage location 174 operably connected to the x-ray system 1000, such as by a suitable wired or wireless connection. With this stored information, in block 212, when the image 106 is accessed and reviewed by an individual or by a post-processing algorithm or the like for a determination of the information in the image 106 for diagnosis purposes, the diagnosis can be performed in part directly on digitized and stored information from the lead marker 104 to assist in the accurate determination of any diagnosis from the image 106 including the lead marker 104.

Some examples of the actions that can be taken by the AI application 102 in blocks 204 and 206 in response to a determination that the image 106 does not contain a lead marker 104 include, but are not limited to the following exemplary cases and combinations thereof:

A. Case 1: Alert—AI application 102 detects the absence of laterality of other required markers and alerts the user. User can decide to retake exposure or insert post-exposure L or R digital markers into the image 106 using the user interface B. Case 2: Laterality Marker—AI application 102 detects the absence of laterality or other markers and employs laterality detection algorithms to locate the left or side of the image 106 automatically and place the L or R digital markers on the image 106; additionally or alternatively alerts the user to get confirmation of type and placement of digital lead marker.

C. Case 3: Expiration Marker—most thoracic exams are done with patient inspiration to reduce motion artifacts, but some procedures are explicitly called out to be carried in expiration state. It is common practice to use EXPIRATION lead marker to indicate to the radiologist that image was taken expiration. The AI application 102 can check for presence or absence of such a marker for an image 106 identified as an expiration image utilizing information, both from the image 106 and optionally from an ancillary sensor source, such as a camera (not shown) that the image 106 should contain the EXPIRATION marker and subsequently alert the user or automatically place the missing marker. The exact imaging condition can be determined by other image quality check algorithms (inspiration/expiration check algorithms).

D. Case 4: Portable Marker—the AI application 102 can detect missing markers and add PORTABLE lead marker automatically into images 106 obtained from portable x-ray devices E. Case 5: Standing vs Supine vs Prone vs Decubitus (Patient Position) Markers—the AI application 102 can detect the absence of any patient position markers and automatically insert them, where the actual patient position in the image 106 can be inferred through protocols used in the taking of the image 106 that are stored in associated with the images 106 and accessible by the AI application 102, as well as any available anatomy/view detection algorithms applied to either x-ray or optical camera images to determine the position of the patient in the image 106

F. Case 6: Weight-Bearing Marker—the AI application 102 can detect the absence of "WEIGH BR" marker. Often the procedures done with weight bearing anatomies like knees are marked as such for radiologist's information during review; additionally any available anatomy/view detection algorithms applied to optical/camera images of the patient can help determine this information to automatically insert markers G. Case 7: Date/Time Markers—the AI application 102 can detect the absence of any required date/time marker and can insert the date/time marker Alternatively to detecting the absence of a required lead marker 104, in block 202 the AI application 102 can determine that a representation of a physical lead marker 104 is present within the image 106. In this situation, the AI application 102 proceeds to block 208 to determine what information is provided by the marker 104, e.g., compare the detected representation of the physical lead marker 104 with a database (not shown) of known physical marker representations and associated definitions or associated information, and digitize the information provided by or otherwise associated with the marker 104 in order to make that information available to other workflow and analysis processes employed regarding the image 106. Some examples of the actions that can be taken by the AI application 102 in block 208 in response to a determination that the image 106 contains a lead marker 104 include, but are not limited to the following exemplary cases and combinations thereof:

- A. Case 1: Initials of Radiographer Name—when the AI application 102 detects a marker(s) 104 indicating the radiographer initials, the AI application 102 can digitize them for use in downstream quality applications, including but not limited to, a "Repeat/Reject Analysis" reporting tool
- B. Case 2: Inspiration/Expiration Markers—when the AI application 102 detects INSPIRATION/EXPIRATION markers 104, the AI application 102 digitizes that information to be employed by downstream clinical AI applications, e.g., a pneumothorax size estimation algorithm that requires the inspiration/expiration status of the image 106 in order to accurately estimate the size of any pneumothorax present in the image 106.
- C. Case 3: Portable Marker—when the AI application 102 detects a PORTABLE marker in the image 106, the digitization of this information can help infer the frontal view position of chest x-ray image 106 (anterior/posterior (AP) vs posterior/anterior (PA)) and can further help with the employment of downstream quantification algorithms, e.g., a cardio-thoracic ratio estimator, to the image 106.
- D. Use Case 4: Standing vs Supine Markers—when the AI application 102 detects a Patient Position marker in the image 106, the digitization of this information, such as for chest x-rays, can be useful in accurately estimating the severity abdominal free air utilizing a detection algorithm as the relative size and volume of free air varies depending on patient position.

Looking now at FIGS. 3A-3H, in the process for the determination by the AI application 102 of the presence or absence of the lead marker 104 in the image 106, a number of pairs of images 106 are illustrated including input images 106' (FIGS. 3A, 3C, 3E, 3G) and associated output or digitized images 106" (FIGS. 3B, 3D, 3F, 3H). In the input image 106', which are the actual X-ray images 106 produced by the X-ray system 1000, the AI application 102 analyzes the input image 106' using any suitable image review process or method, in order to determine the presence, location and shape/configuration of any lead markers 104 in the image 106'. Using the image review process, the AI application 102 locates the pixels in the image 106' that represent the physical lead marker 104, as shown in the output image 106". Using the information concerning the location and shape of the pixels forming the marker 104, or using other information regarding the image 106 from outside the image 106 in the case of an absent marker 104, as described previously, the AI application 102 can discern and digitize the information supplied by the lead marker 104 for storage in storage device or location 170 and/or 174, or in another electronic storage device or media, in association with the image 106' for further processing of the image 106'. Further, the digitization of the lead marker 108" in the image 106", whether done from a lead marker 104 present in the image 106 or being a lead marker 104 inserted in the image 106, enables the AI application 102 to position or reposition the lead marker 108" as necessary so as not to obscure the image 106" and avoid the marker 108" being treated as an artefact.

Finally, it is also to be understood that the system 1000 may include the necessary computer, electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor/processing unit/computer and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application(s)/algorithm(s) that adapts the computer/controller to perform the methods disclosed herein may be read into a main memory of the at least one processor from a computer-readable medium. The term "computer-readable medium", as used herein, refers to any medium that provides or participates in providing instructions to the at least one processor of the system 1000 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method of determining the presence of lead markers in an X-ray image comprising the steps of:
   providing an X-ray system comprising:
      an X-ray source; and
      an X-ray detector positionable in alignment with the X-ray ray source; and
      a processing unit operably connected to the X-ray source and the X-ray detector to produce X-ray images from data transmitted from the X-ray detector, wherein the processing unit includes a lead marker detection system configured to detect representations of physical lead markers in the X-ray images; and
   applying the lead marker detection system to the X-ray images,
   wherein the representation of the physical lead marker is a representation of a patient position lead marker or a representation of an expiration lead marker.

2. The method of claim 1, wherein the step of applying the lead marker detection system comprises detecting the presence or absence of the representations of a physical lead marker within an X-ray image.

3. The method of claim 2, further comprising the step of inserting a digital lead marker within the X-ray image.

4. The method of claim 3, wherein the step of inserting the digital lead marker in the X-ray image comprises the steps of:
   detecting the absence of the representation of a physical lead marker in the X-ray image;
   determining one or more characteristics of the X-ray image; and
   inserting one or more digital lead markers corresponding to the characteristics of the X-ray image within the X-ray image.

5. The method of claim 4, further comprising the step of displaying the X-ray image with the digital lead marker for review.

6. The method of claim 4, further comprising the step of storing information corresponding to the digital lead marker in association with the X-ray image.

7. The method of claim 6, further comprising the step of accessing the stored X-ray image and information corresponding to the digital lead marker for post-processing diagnostic purposes.

8. The method of claim 4, further comprising the step of providing an alert regarding the detected absence of the representation of the physical lead marker.

9. The method of claim 4, wherein the step of determining the one or more characteristics of the X-ray image comprises accessing protocols employed by the X-ray system in obtaining the X-ray image.

10. The method of claim 9, wherein the step of determining the one or more characteristics of the X-ray image comprises at least one of the steps of:
    determining a type of X-ray system employed to obtain the X-ray image;
    determining a type of X-ray exam performed by obtaining the X-ray image;
    determining a time parameter when the X-ray image was obtained; and
    determining a user that operated the X-ray system to obtain the X-ray image.

11. The method of claim 9, wherein the step of storing information corresponding to the detected physical lead marker comprises the steps of:
    digitizing the one or more characteristics of the X-ray image; and
    storing the digitized characteristics of the X-ray image in association with the X-ray image.

12. The method of claim 11, further comprising the step of accessing the stored X-ray image and the digitized characteristics of the X-ray image for post-processing diagnostic purposes.

13. The method of claim 2, wherein the step of detecting the presence or absence of the representation of the physical lead marker in the X-ray image comprises the steps of:
    detecting the presence of the representation of a physical lead marker in the X-ray image;
    determining one or more characteristics of the X-ray image from the representation of the physical lead marker in the X-ray image; and
    storing information corresponding to the detected physical lead marker in association with the X-ray image.

14. The method of claim 2, further comprising the steps of:
    digitizing one or more characteristics of the X-ray image, the representation of the physical lead marker in the X-ray image, and combinations thereof; and
    storing the digitized characteristics in association with the X-ray image.

15. An X-ray system comprising:
    an X-ray source;
    an X-ray detector positionable in alignment with the X-ray ray source; and
    a processing unit operably connected to the X-ray source and the X-ray detector to produce X-ray images from data transmitted from the X-ray detector,
    wherein the processing unit includes lead marker detection system configured to detect a presence or an absence of representations of physical lead markers within the X-ray images,
    wherein the representation of the physical lead marker is a representation of a patient position lead marker or a representation of an expiration lead marker.

16. The X-ray system of claim 15, wherein the lead marker detection system is configured to detect the presence of the representation of a physical lead marker in the X-ray image, to determine one or more characteristics of the X-ray image from the representation of the physical lead marker in the X-ray image; and to store information corresponding to the detected physical lead marker in association with the X-ray image.

17. The X-ray system of claim 15, wherein the lead marker detection system is configured to detect the absence of the representation of a physical lead marker in the X-ray image, to determine one or more characteristics of the X-ray image and to insert one or more digital lead markers corresponding to the characteristics of the X-ray image within the X-ray image.

18. The X-ray system of claim 17, wherein the lead marker detection system is configured to store information corresponding to the digital lead marker in association with the X-ray image.

19. The X-ray system of claim 17, wherein the lead maker detection system is configured to determine the one or more characteristics of the X-ray image by accessing protocols employed by the X-ray system in obtaining the X-ray image.

20. The X-ray system of claim 17, wherein the lead marker detection system is configured to determine the one or more characteristics of the X-ray image by at least one of:
    determining a type of X-ray system employed to obtain the X-ray image;

determining a type of X-ray exam performed by obtaining the X-ray image;
determining a time parameter when the X-ray image was obtained; and
determining a user that operated the X-ray system to obtain the X-ray image.

\* \* \* \* \*